(12) United States Patent
Zhang et al.

(10) Patent No.: US 11,465,995 B2
(45) Date of Patent: Oct. 11, 2022

(54) CRYSTAL AND SALT FORMS OF TRICYCLIC COMPOUND AND PREPARATION PROCESS THEREOF

(71) Applicant: SHIJIAZHUANG SAGACITY NEW DRUG DEVELOPMENT COMPANY, LTD., Hebei (CN)

(72) Inventors: Peng Zhang, Shanghai (CN); Weidong Li, Shanghai (CN); Lingyun Wu, Shanghai (CN)

(73) Assignee: Medshine Discovery Inc., Jiangsu (CN)

( * ) Notice: Subject to any disclaimer, the term of this patent is extended or adjusted under 35 U.S.C. 154(b) by 193 days.

(21) Appl. No.: 16/963,005

(22) PCT Filed: Jan. 18, 2019

(86) PCT No.: PCT/CN2019/072374
§ 371 (c)(1),
(2) Date: Jul. 17, 2020

(87) PCT Pub. No.: WO2019/141245
PCT Pub. Date: Jul. 25, 2019

(65) Prior Publication Data
US 2020/0339553 A1    Oct. 29, 2020

(30) Foreign Application Priority Data

Jan. 18, 2018  (CN) .......................... 201810049853.2

(51) Int. Cl.
*C07D 413/10*  (2006.01)
*A61P 1/00*  (2006.01)

(52) U.S. Cl.
CPC .............. *C07D 413/10* (2013.01); *A61P 1/00* (2018.01); *C07B 2200/13* (2013.01)

(58) Field of Classification Search
CPC ...... C07D 413/10; A61P 1/00; C07B 2200/13
See application file for complete search history.

(56) References Cited

U.S. PATENT DOCUMENTS

2021/0300908 A1* 9/2021 Wu ...................... C07D 209/58

FOREIGN PATENT DOCUMENTS

| CN | 102099333 A | 6/2011 |
| CN | 102762100 A | 10/2012 |
| CN | 103298807 A | 9/2013 |
| CN | 103380112 A | 10/2013 |
| EP | 3492465 A1 | 6/2019 |
| WO | 2011060392 A1 | 5/2011 |
| WO | 2018014862 | 1/2018 |

OTHER PUBLICATIONS

Jul. 30, 2021 Extended European Search Report issued in European Patent Application No. 19740931.1.
Aug. 25, 2021 the First Office Action issued in Chinese Patent Application No. 2019800087985.
International Search Report dated Apr. 16, 2019 in corresponding International Application No. PCT/CN2019/072374.
Written Opinion dated Apr. 16, 2019 in corresponding International Application No. PCT/CN2019/072374.
Apr. 5, 2022 European Office Action issued in European Patent Application No. 19740931.1.
Mar. 22, 2022 Indian Office Action issued in Indian Patent Application No. 202017035143.

* cited by examiner

*Primary Examiner* — Timothy R Rozof
(74) *Attorney, Agent, or Firm* — Ice Miller LLP (57) ABSTRACT

Provided are a crystal form of a tricyclic compound and a preparation process thereof. Also provided is an application of the crystal form in preparing a drug for treating a disease related to a sphingosine-1-phosphate subtype 1 (S1P1) receptor.

Compound 1

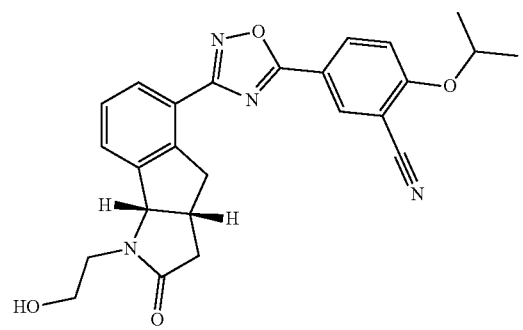

(1)

19 Claims, 2 Drawing Sheets

CRYSTAL AND SALT FORMS OF TRICYCLIC COMPOUND AND PREPARATION PROCESS THEREOF

CROSS-REFERENCE TO RELATED APPLICATION

This application is a Section 371 of International Application No. PCT/CN2019/072374, filed Jan. 18, 2019, which was published in the Chinese language on Jul. 25, 2019, under International Publication No. WO 2019/141245 A1, which claims priority under 35 U.S.C. § 119(b) to Chinese Patent Application No. 201810049853.2, filed on Jan. 18, 2018, the disclosures of which are incorporated herein by reference in their entireties.

TECHNICAL FIELD

Provided are a Crystal Form of a tricyclic compound and preparing process thereof as well as use of the Crystal Form for the manufacture of a medicament for treating a disease associated with S1P1 receptor.

BACKGROUND

Sphingosine 1-phosphate (S1P) is a versatile lipid mediator with broad physiological activities, including cell proliferation, survival, lymphocyte transport, cytoskeletal organization and morphogenesis. Sphingosine is catalyzed by the enzyme of ceramide and released from ceramide. With the catalysis of sphingosine kinase, sphingosine is phosphorylated to produce sphingosine 1-phosphate (S1P) and interacts with sphingosine 1-phosphate receptor (S1PR) to produce physiological activity.

Sphingosine 1-phosphate receptor 1 (S1PR1), also known as endothelial cell differentiation gene 1 (EDG1), is a G protein-coupled receptor, belongs to the endothelial cell differentiation gene (EDG) receptor family and is a protein encoded by the S1PR1 gene. Sphingosine 1-phosphate receptor (S1PR) includes five subtypes (S1PR 1-5), of which sphingosine 1-phosphate receptor 1 (S1PR1) is abundantly distributed on the endothelial cell membrane. Like other G protein-coupled receptors, S1PR1 detects its ligands from outside of the cell and activates intracellular signaling pathways to give cellular responses.

Sphingosine 1-phosphate (S1P) plays a very important role in human body and mainly regulates the vascular system and immune system. Small molecule S1P1 agonists and inhibitors mimic the binding mechanism of sphingosine 1-phosphate (S1P) to receptors and have been proved to play important physiological roles in the signaling systems. Agonism of Sphingosine 1-phosphate receptor 1 (S1PR1) will disrupt lymphocyte transport, isolating lymphocytes in lymph nodes and other secondary lymphoid organs and resulting in rapid and reversible lymphopenia. Clinical studies have shown that lymphocyte isolation reduces inflammation or autoimmune disease response and is essential for immune regulation.

Currently, published in vivo pharmacodynamic studies of sphingosine 1-phosphate receptor 1 (S1PR1) agonists are used for treating or preventing autoimmune diseases. The discovery and application of new sphingosine 1-phosphate receptor 1 (S1PR1) agonists is promising. Ozanimod is an S1PR1 agonist with the following structure.

Ozanimod

SUMMARY

In an aspect, provided is a Crystal Form A of Compound 1, wherein the Crystal Form A has an X-ray powder diffraction pattern having characteristic diffraction peaks at the following 2θ angles: 6.66±0.2°, 13.30±0.2°, 15.57±0.2°.

Compound 1

In some embodiments according to the present disclosure, the Crystal Form A of Compound 1 has an X-ray powder diffraction pattern having characteristic diffraction peaks at the following 2θ angles: 6.66±0.2°, 13.30±0.2°, 14.46±0.2°, 15.57±0.2°, 19.99±0.2°, 21.83±0.2°, 24.41±0.2°, 25.26±0.2°.

In some embodiments according to the present disclosure, the Crystal Form A of Compound 1 has an X-ray powder diffraction pattern having characteristic diffraction peaks at the following 2θ angles: 6.66±0.2°, 12.21±0.2°, 13.30±0.2°, 14.46±0.2°, 15.57±0.2°, 16.77±0.2°, 19.99±0.2°, 21.83±0.2°, 24.41±0.2°, 25.26±0.2°, 27.20±0.2°.

Figure 1:
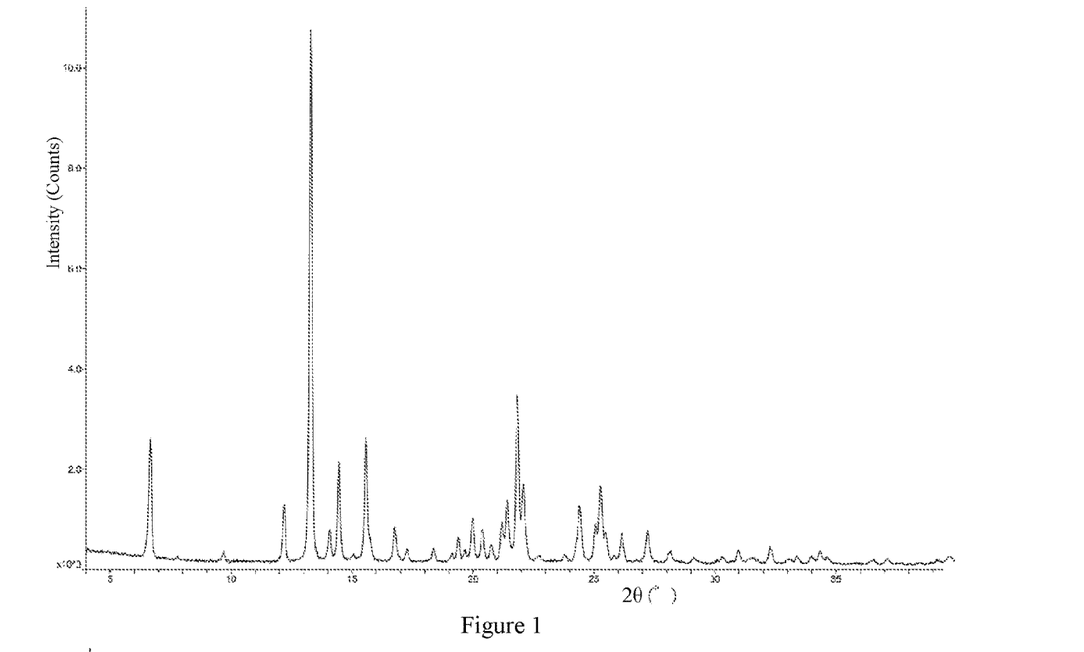
FIG. 1 shows the XRPD pattern by Cu—Kα radiation of the Crystal Form A of Compound 1.

In some embodiments according to the present disclosure, the Crystal Form A of Compound 1 has an XRPD pattern as shown in FIG. 1.

TABLE 1

XRPD Pattern Analysis Data of Crystal Form A of Compound 1

| No | 2θ angle (°) | Inter-planar spacing (Å) | Height (Intensity) | Relative Height (%) | Area | Relative Area (%) |
|---|---|---|---|---|---|---|
| 1 | 6.665 | 13.2510 | 2370 | 22.4 | 18988 | 23.8 |
| 2 | 12.211 | 7.2424 | 1123 | 10.6 | 8542 | 10.7 |
| 3 | 13.299 | 6.6523 | 10595 | 100.0 | 79737 | 100 |
| 4 | 14.086 | 6.2823 | 590 | 5.6 | 4885 | 6.1 |
| 5 | 14.463 | 6.1194 | 1951 | 18.4 | 15218 | 19.1 |
| 6 | 15.569 | 5.6871 | 2445 | 23.1 | 21976 | 27.6 |

TABLE 1-continued

XRPD Pattern Analysis Data of Crystal Form A of Compound 1

| No | 2θ angle (°) | Inter-planar spacing (Å) | Height (Intensity) | Relative Height (%) | Area | Relative Area (%) |
|---|---|---|---|---|---|---|
| 7  | 16.771 | 5.2819 | 683  | 6.4  | 5503  | 6.9  |
| 8  | 19.987 | 4.4387 | 824  | 7.8  | 8038  | 10.1 |
| 9  | 20.383 | 4.3534 | 554  | 5.2  | 4198  | 5.3  |
| 10 | 21.213 | 4.1849 | 734  | 6.9  | 9023  | 11.3 |
| 11 | 21.430 | 4.1429 | 1191 | 11.2 | 15988 | 20.1 |
| 12 | 21.828 | 4.0683 | 3282 | 31.0 | 33217 | 41.7 |
| 13 | 22.082 | 4.0221 | 1484 | 14.0 | 26260 | 32.9 |
| 14 | 24.412 | 3.6433 | 1098 | 10.4 | 11242 | 14.1 |
| 15 | 25.065 | 3.5498 | 699  | 6.6  | 11405 | 14.3 |
| 16 | 25.263 | 3.5224 | 1472 | 13.9 | 21602 | 27.1 |
| 17 | 25.495 | 3.4909 | 553  | 5.2  | 13621 | 17.1 |
| 18 | 26.149 | 3.4051 | 548  | 5.2  | 4624  | 5.8  |
| 19 | 27.198 | 3.2760 | 650  | 6.1  | 6723  | 8.4  |
| 20 | 28.160 | 3.1663 | 236  | 2.2  | 3047  | 3.8  |
| 21 | 30.985 | 2.8837 | 251  | 2.4  | 3429  | 4.3  |
| 22 | 32.272 | 2.7716 | 339  | 3.2  | 3041  | 3.8  |
| 23 | 34.342 | 2.6091 | 244  | 2.3  | 5904  | 7.4  |
| 24 | 34.622 | 2.5886 | 143  | 1.3  | 3113  | 3.9  |

In some embodiments according to the present disclosure, the Crystal Form A of Compound 1 has a differential scanning calorimetry curve having onset point of endothermic peak at 199.27° C.±2° C.

Figure 2:
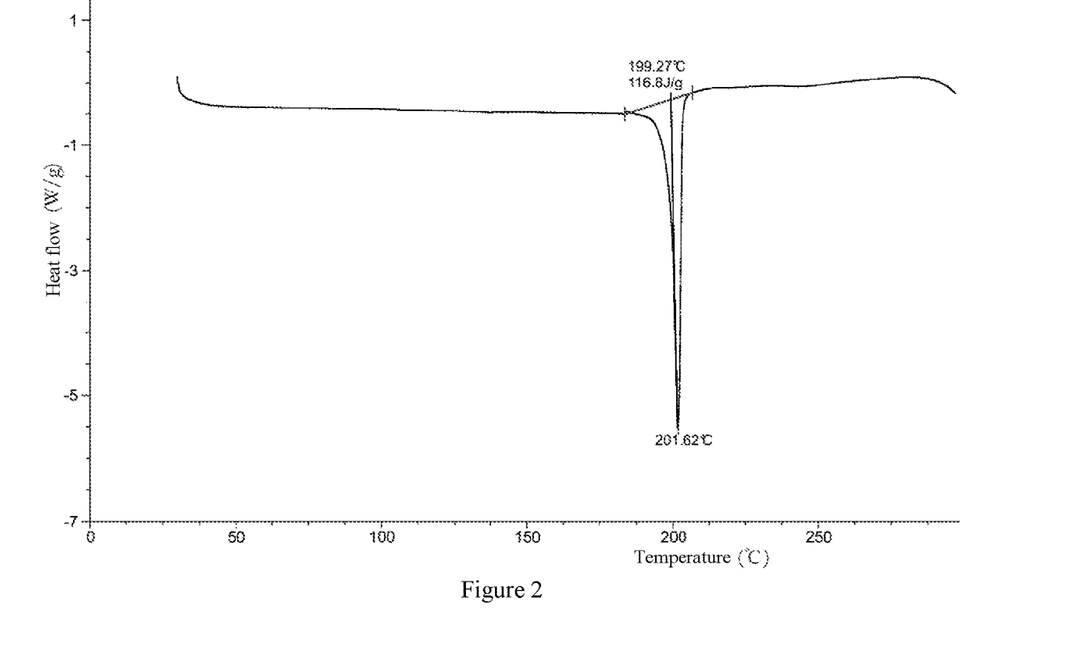
FIG. 2 shows the DSC pattern of the Crystal Form A of Compound 1.

In some embodiments according to the present disclosure, the Crystal Form A of Compound 1 has a DSC pattern as shown in FIG. 2.

In some embodiments according to the present disclosure, the Crystal Form A of Compound 1 has a thermogravimetric analysis curve wherein no significant weight loss occurs prior to 251.39° C., and decomposition occurs after 251.39° C.

Figure 3:
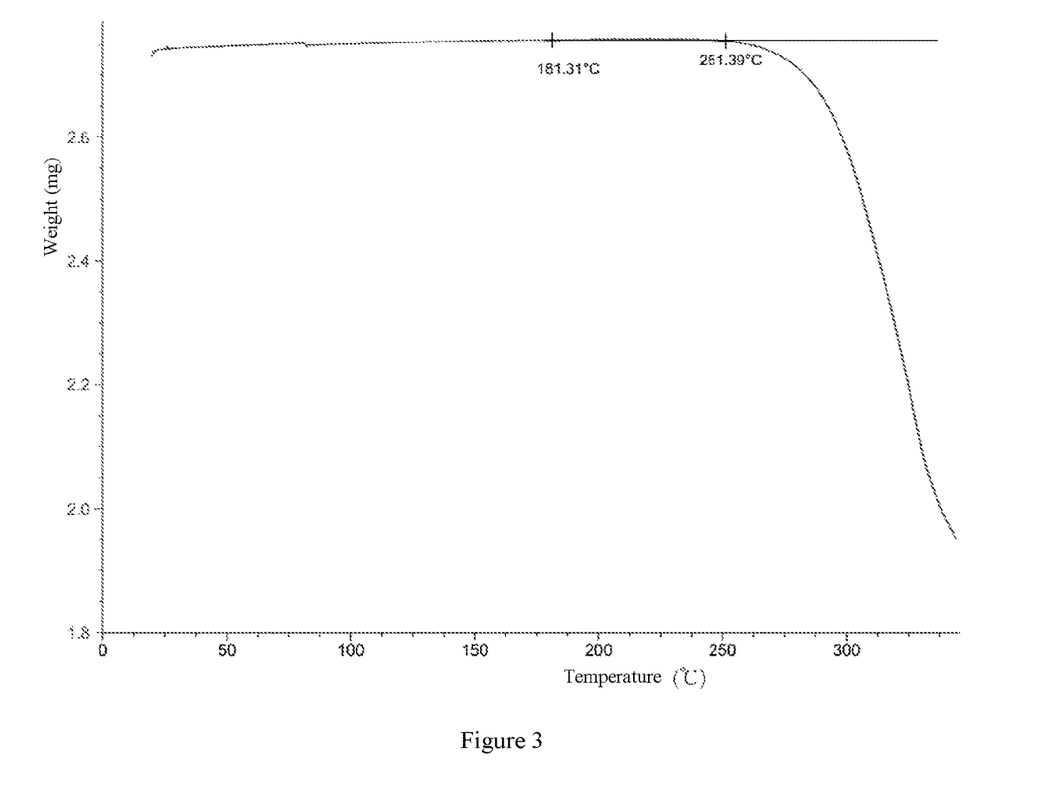
FIG. 3 shows the TGA pattern of the Crystal Form A of Compound 1.

In some embodiments according to the present disclosure, the Crystal Form A of Compound 1 has a TGA pattern as shown in FIG. 3.

In another aspect, provided is a process for preparing the Crystal Form A, comprising adding the Compound 1 into acetonitrile, an alcohol solvent, a ketone solvent, an ester solvent, an ether solvent, a mixed solvent of alcohol solvent and water, a mixed solvent of acetonitrile and water, a mixed solvent of ketone solvent and water, or a mixed solvent of ether solvent and water; and recrystallizing or slurrying to obtain the Crystal Form A.

In some embodiments according to the present disclosure, the alcohol solvent is selected from the group consisting of methanol, ethanol and isopropanol.

In some embodiments according to the present disclosure, the ketone solvent is selected from the group consisting of acetone and butanone.

In some embodiments according to the present disclosure, the ether solvent is selected from the group consisting of ethylene glycol dimethyl ether.

In some embodiments according to the present disclosure, the ester solvent is selected from the group consisting of ethyl acetate.

In some embodiments according to the present disclosure, the mixed solvent of alcohol solvent and water is a mixed solvent of ethanol and water, a mixed solvent of methanol and water, or a mixed solvent of isopropanol and water.

In some embodiments according to the present disclosure, the mixed solvent of ketone solvent and water is selected from the group consisting of a mixed solvent of acetone and water.

In some embodiments according to the present disclosure, in the mixed solvent of alcohol solvent and water, the volume ratio of alcohol solvent to water is selected from the group consisting of 1:0.2-1.5.

In some embodiments according to the present disclosure, in the mixed solvent of ketone solvent and water, the volume ratio of ketone solvent to water is selected from the group consisting of 1:0.3-0.8.

In some embodiments according to the present disclosure, in the mixed solvent of acetonitrile and water, the volume ratio of acetonitrile to water is selected from the group consisting of 1:0.5-1.5.

In yet another aspect, provided is use of the Crystal Form A of Compound 1 for the manufacture of a medicament for treating a disease associated with S1P1 receptor.

In some embodiments according to the present disclosure, the disease associated with S1P1 receptor is inflammatory bowel disease.

Technical Effect

The Crystal Form A of Compound 1 has good stability, low hygroscopicity and promising druggability. The Crystal Form A provided herein has good stability and is easy for formulation into a medicament. Compound 1 has significant inhibitory effect on S1P1 related pathways. It is found in the TNBS-induced SD rat model of acute infectious bowel disease that the Crystal Form A of Compound 1 has a significant inhibitory effect on ulcerative colitis. Compound 1 can significantly improve one or more indicators of rat pharmacokinetics as compared to Ozanimod.

General Definition

Unless stated otherwise, the following terms and phrases have the following definitions. A specific term or phrase should not be considered as indefinite or unclear without specific definition and should be understood according to the normal meanings. A tradename used herein shall refer to the corresponding article or the active ingredient.

The intermediate compounds herein can be prepared by various synthesis processes well-known to a person skilled in the art, including the specific embodiments listed below, the embodiments by a combination with other chemical synthesis processes, and equivalent alternatives well known to a person skilled in the art. The preferable embodiments include but are not limited to the Examples below.

The chemical reaction of the specific embodiments is performed in a suitable solvent, and the solvent should be suitable for the chemical changes of the present disclosure and the required reagents and materials. To obtain the compound of the present disclosure, a person skilled in the art can modify or select a synthesis step or a reaction scheme based on the available embodiments.

The present disclosure will be described in a detailed manner and the Examples should be not considered as limitation thereto.

The solvents used herein are commercially available and can be used without further purification.

The following abbreviations are used: DMF: dimethylformamide; MsOH: methane sulfonic acid; EtOH: ethanol; NaOH: sodium hydroxide; M: mol/L.

The compounds are named manually or by ChemDraw® software. The compound names on catalog by the providers are used.

X-ray Powder Diffractometer, XRPD

Testing method: about 10-20 mg of sample is used for XRPD detection.

Detailed XRPD parameters are as follows:
Light tube: Cu, kα, (λ=1.54056Å).
Light tube voltage: 40 kV, Light tube current: 40 mA
Divergence slit: 0.60 mm
Detector slit: 10.50 mm
Anti-scatter slit: 7.10 mm
Scanning range: 4-40 deg
Step size: 0.02 deg
Time/step: 0.12 s
Sample stage spinning speed: 15 rpm
Differential Scanning Calorimeter, DSC Testing method: The sample (about 1 mg) is placed in DSC aluminum pot for testing, under 50 mL/min $N_2$, with the heating rate of 10° C./min, and the sample is heated from room temperature to 300° C.
Thermal Gravimetric Analyzer, TGA Testing method: The sample (2-5 mg) is placed in TGA platinum pot for testing, under 25 mL/min $N_2$, with the heating rate of 10° C./min, and the sample is heated from room temperature to 20% weight loss.

EXAMPLES

The following Examples are provided for further illustration for the purpose of better understanding of the present disclosure. The specific embodiments should not be understood as limitation to the present disclosure.

Example 1

Preparation of Compound 1

-continued

Step 1

Compound 1-1 (20.0 g, 94.8 mmol) was dissolved in anhydrous tetrahydrofuran (200 mL), to which was added dropwise lithium bis(trimethylsilyl)amide (1 M tetrahydrofuran solution, 113 mL) at −78° C. The reaction was stirred at that temperature for 30 min. To the reaction solution was added ethyl bromoacetate (17.4 g, 104 mmol) and the reaction solution was stirred at 25° C. for 2 hours. To the reaction solution was added water (200 mL), which was extracted with ethyl acetate (200 mL×3). The organic phases were combined and washed with saturated saline solution (300 mL×2), dried over anhydrous sodium sulfate, and filtered. The filtrate was concentrated under reduced pressure. The residue was isolated and purified with silica gel column chromatography (10:1 petroleum ether/ethyl acetate, Rf=0.7) to give Compound 1-2 (15.0 g, as yellowish oil). Yield: 53%.

$^1$H NMR: (400 MHz, CDCl$_3$) δ7.87 (d, J=8.0 Hz, 1H), 7.71 (d, J=8.0 Hz, 1H), 7.38 (t, J=8.0 Hz, 1H), 4.11 (q, J=6.8 Hz, 2H), 3.33-3.10 (m, 1H), 2.96-2.87 (m, 2H), 2.69-2.65 (m, 2H), 1.19 (t, J=6.8 Hz, 3H). MS-ESI Calculated: [M+H]$^+$ 297 and 299, Found: 297 and 299.

Step 2

Compound 1-2 (25.0 g, 84.1 mmol) was dissolved in anhydrous ethanol (300 mL), to which was added ammonium acetate (64.9 g, 841 mmol) at 25° C. The reaction was stirred at that temperature for 1 h. To the reaction solution was added sodium cyanoborohydride (15.9 g, 252 mmol) and the reaction solution was stirred at 80° C. for 12 h. To the reaction solution was added water (300 mL), which was extracted with ethyl acetate (400 mL×3). The organic phases were combined and washed with saturated saline solution (300 mL×2), dried over anhydrous sodium sulfate, and filtered. The filtrate was concentrated under reduced pressure. The residue was isolated and purified with silica gel column chromatography (10:1 ethyl acetate/methanol, Rf=0.4) to give Compound 1-3 (10.0 g, as yellowish oil). Yield: 47%. MS-ESI Calculated: [M+H]$^+$ 252 and 254, Found: 252 and 254.

Step 3

Compound 1-3 (10.0 g, 39.7 mmol) was dissolved in anhydrous N,N-dimethylformamide (80 mL), to which was added sodium hydride (2.38 g, 59.5 mmol, 60% purity) in portions at 0° C. The reaction was stirred at that temperature for 30 min. To the reaction solution was added Compound 1-4 (9.49 g, 39.7 mmol) and the reaction solution was stirred at 25° C. for 2 h. To the reaction solution was added water (200 mL), which was extracted with ethyl acetate (200 mL×3). The organic phases were combined and washed with saturated saline solution (300 mL×2), dried over anhydrous sodium sulfate, and filtered. The filtrate was concentrated under reduced pressure. The residue was isolated and purified with silica gel column chromatography (1:1 petroleum ether/ethyl acetate, Rf=0.5) to give Compound 1-5 (5.00 g, as colorless oil). Yield: 31%.

$^1$H NMR: (400 MHz, d$_4$-MeOH) δ7.46-7.42 (m, 2H), 7.12 (d, J=8.0 Hz, 1H), 5.17 (d, J=7.2 Hz, 1H), 3.70-3.67 (m, 3H), 3.24-3.23 (m, 1H), 3.18-3.16 (m, 2H), 2.70-2.68 (m, 2H), 2.34-2.33 (m, 1H), 0.84 (s, 9H), 0.01 (s, 6H). MS-ESI Calculated: [M+H]$^+$ 410 and 412, Found: 410 and 412.

Step 4

Compound 1-5 (5.00 g, 12.2 mmol) was dissolved in N,N-dimethylformamide (8 mL). To the reaction solution were added zinc cyanide (2.86 g, 24.4 mmol) and tetratriphenylphosphine palladium (1.41 g, 1.22 mmol), which was stirred under nitrogen protective atmosphere at 100° C. for 16 h. The reaction solution was cooled to room temperature, and was added with water (30 mL) and extracted with ethyl acetate (50 mL×3). The organic phases were combined and washed with saturated saline solution (40 mL×3), dried over anhydrous sodium sulfate, and filtered. The filtrate was concentrated under reduced pressure. The residue was isolated and purified with silica gel column chromatography (1:1 petroleum ether/ethyl acetate, Rf=0.4) to give Compound 1-6 (3.10 g, as colorless oil). Yield: 71%.

$^1$H NMR: (400 MHz, d$_4$-MeOH) δ7.87 (d, J=8.0 Hz, 1H), 7.70 (d, J=8.0 Hz, 1H), 7.47 (t, J=8.0 Hz, 1H), 5.26 (d, J=7.2 Hz, 1H), 3.82-3.70 (m, 3H), 3.51-3.49 (m, 1H), 3.30-3.27 (m, 1H), 3.01-2.81 (m, 3H), 2.45-2.41 (m, 1H), 0.93 (s, 9H), 0.00 (s, 6H). MS-ESI Calculated: [M+H]$^+$ 357, Found: 357.

Step 5

Compound 1-6 (3.00 g, 8.41 mmol) was dissolved in anhydrous ethanol (8 mL). To the reaction solution were added hydroxylamine hydrochloride (1.75 g, 25.2 mmol) and triethylamine (3.40 g, 33.6 mmol). The reaction solution was stirred under nitrogen protective atmosphere at 60° C. for 12 h. The reaction solution was cooled to room temperature, and was added with water (50 mL) and extracted with ethyl acetate (50 mL×3). The organic phases were combined and washed with saturated saline solution (40 mL×2), dried over anhydrous sodium sulfate, and filtered. The filtrate was concentrated under reduced pressure. The residue was isolated and purified with silica gel column chromatography (0:1 petroleum ether/ethyl acetate, Rf=0.4) to give Compound 1-7 (3.00 g, as white solid). Yield: 92%.

$^1$H NMR: (400 MHz, CDCl$_3$) δ7.49 (d, J=8.0 Hz, 1H), 7.40 (d, J=8.0 Hz, 1H), 7.21 (t, J=8.0 Hz, 1H), 5.07 (d, J=7.2 Hz, 1H), 4.73 (s, 2H), 3.78-3.76 (m, 1H), 3.67-3.62 (m, 2H), 3.44-3.42 (m, 1H), 2.97-2.90 (m, 3H), 2.71-2.65 (m, 1H), 2.37-2.33 (m, 1H), 0.84 (s, 9H), 0.00 (s, 6H). MS-ESI Calculated: [M+H]$^+$ 390, Found: 390.

Step 6

Compound 1-8 (695 mg, 3.39 mmol) was dissolved in N,N-dimethylformamide (10 mL). To the reaction solution were added 1-hydroxybenzotriazole (763 mg, 5.65 mmol) and 1-(3-dimethylaminopropyl)-3-ethylcarbodiimide hydrochloride (1.08 g, 5.65 mmol). The reaction solution was stirred under nitrogen protective atmosphere at 25° C. for 0.5 h. To the reaction solution was added Compound 1-7 (1.10 g, 2.82 mmol) which was stirred at 25° C. for 1 h and then heated to 80° C., then stirred at 80° C. for 12 h. The reaction solution was cooled to room temperature, and was added with water (30 mL) and extracted with ethyl acetate (30 mL×3). The organic phases were combined and washed with saturated saline solution (25 mL×2), dried over anhydrous sodium sulfate, and filtered. The filtrate was concentrated under reduced pressure. The residue was isolated and purified with silica gel column chromatography to give Compound 1-9

$^1$H NMR: (400 MHz, d$_4$-MeOH) δ8.46-8.42 (m, 2H), 8.19 (d, J=7.2 Hz, 1H), 7.78 (d, J=7.2 Hz, 1H), 7.51-7.44 (m, 2H), 5.26 (d, J=7.2 Hz, 1H), 4.99-4.94 (m, 1H), 3.83-3.71 (m, 4H), 3.26-3.23 (m, 2H), 3.15-3.13 (m, 1H), 2.92-2.86 (m, 1H), 2.48-2.43 (m, 1H), 1.47 (d, J=6.0 Hz, 6H). MS-ESI Calculated: [M+H]$^+$ 445, Found: 445.

Step 7

Compound 1-9 (200 mg, 0.450 mmol) was subjected to chiral liquid chromatography for isolation and purification to give Compound 1-10 and Compound 1.

SFC Separation Method:
Chromatographic column: AD 250 mm×30 mm, 10 μm;
Mobile phase: A: carbon dioxide; B: 45%-45% ethanol (containing 0.1% aqueous ammonia);
Flow rate: 80 mL/min;
Column temperature: 40° C.
Compound 1-10, the retention time in high performance chiral liquid column is 5.276 min.

$^1$H NMR: (400 MHz, d$_4$-MeOH) δ8.42-8.40 (m, 2H), 8.17 (d, J=7.6 Hz, 1H), 7.77 (d, J=7.6 Hz, 1H), 7.50-7.42 (m, 2H), 5.26 (d, J=7.2 Hz, 1H), 4.99-4.95 (m, 1H), 3.81-3.71 (m, 4H), 3.26-3.23 (m, 2H), 3.13-3.08 (m, 1H), 2.92-2.86 (m, 1H), 2.48-2.44 (m, 1H), 1.47 (d, J=6.0 Hz, 6H). MS-ESI Calculated: [M+H]$^+$ 445, Found: 445.

Compound 1, the retention time in high performance chiral liquid column is 6.427 min.

$^1$H NMR: (400 MHz, d$_4$-MeOH) δ8.45-8.42 (m, 2H), 8.19 (d, J=7.6 Hz, 1H), 7.78 (d, J=7.6 Hz, 1H), 7.51-7.44 (m, 2H), 5.27 (d, J=7.2 Hz, 1H), 4.99-4.94 (m, 1H), 3.83-3.71 (m, 4H), 3.26-3.23 (m, 2H), 3.15-3.13 (m, 1H), 2.92-2.88 (m, 1H), 2.48-2.44 (m, 1H), 1.47 (d, J=6.0 Hz, 6H). MS-ESI Calculated: [M+H]$^+$ 445, Found: 445.

Example 2

Preparation of Crystal Form A of Compound 1

To ethanol (2 L) was added Compound 1 (80 g), which was heated to 80° C. and stirred for 96 h. The system was cooled to room temperature and filtered. The filter cake was collected and dried under vacuum to give Crystal Form A of Compound 1.

About 50 mg of Compound 1 was taken into sample bottles, to which were added the solvents or mixed solvents in the following table. The bottles were shaken at 40° C. for two consecutive days and then centrifuged. The residual solids as obtained above were collected and dried under vacuum at 40° C. overnight to give Crystal Form A of Compound 1.

| No. | Solvent |
| --- | --- |
| 1 | methanol |
| 2 | ethanol |
| 3 | acetonitrile |
| 4 | acetone |
| 5 | ethyl acetate |
| 6 | tetrahydrofuran |
| 7 | dioxane |
| 8 | water |
| 9 | methanol-water (3:1) |
| 10 | ethanol-water (3:1) |
| 11 | acetonitrile-water (1:1) |
| 12 | acetone-water (1:2) |

About 30 mg of Compound 1 was taken into a sample bottle, to which was added 4 mL of tetrahydrofuran, and ultrasonically solubilized for 5 min. The sample was stirred on a magnetic stirrer for 1 h at 50° C. The supernatant was collected into a bottle and the bottle opening was covered with aluminum foil and pierced with some small holes. The bottle was placed in a fume hood to allow the sample to spontaneously evaporate (in darkness). The resulting residual solids were dried under vacuum at room temperature overnight, and then placed in a 30° C. vacuum drying oven for 4 h to give Crystal Form A of Compound 1.

About 30 mg of Compound 1 was taken into a sample bottle, to which was added 4 mL of acetone, and ultrasonically solubilized for 30 min. The sample was stirred on a magnetic stirrer for 1 h at 50° C. 2 mL of acetone was added. Stirring was continued. The sample was filtered after 30 min while it was hot. The filtrate was collected into a glass bottle and the bottle opening was covered with aluminum foil and pierced with some small holes. The bottle was placed in a fume hood to allow the sample to spontaneously evaporate (in darkness). The resulting residual solids were dried under vacuum at room temperature overnight, and then placed in a 30° C. vacuum drying oven for 4 h to give Crystal Form A of Compound 1.

About 30 mg of Compound 1 was taken, to which was added 2 mL of tetrahydrofuran, and ultrasonically solubilized for 30 min. The sample was stirred on a magnetic stirrer for 1 h at 50° C. in darkness. After 1 h, 1 mL of tetrahydrofuran was added. Stirring was continued. The sample liquid was filtered after 30 min while it was hot. The filtrate was placed in a glass bottle and the sample liquid was placed and cooled in a refrigerator at −5° C. White solids precipitated after 3 days. The sample was centrifuged, and the supernatant was discarded. The solids were placed in a 30° C. vacuum drying oven overnight to give Crystal Form A of Compound 1.

Experimental Example 1

Stability Test of Crystal Form A Solid

Crystal Form A was placed in an opening container with constant temperature and humidity for accelerated test, under the conditions of 40° C./75% humidity (open). Samples were taken at $1^{st}$, $2^{nd}$, $3^{rd}$ month for testing, and the test results were compared with initial results of day 0. The test results were shown in Table 2 below:

TABLE 2

Stability test of Crystal Form A solid

| Testing conditions | Time point for sampling (month) | Appearance | Content (%) | Total Impurity (%) |
|---|---|---|---|---|
| Initial | 0 | White powder | 101.6 | 0.33 |
| 40° C./75% humidity (Open) | 1 | White powder | 101.4 | 0.31 |
| 40° C./75% humidity (Open) | 2 | White powder | 98.8 | 0.34 |
| 40° C./75% humidity (Open) | 3 | White powder | 101.8 | 0.32 |

Analyzing Method:

| Device | Agilent 1200 High Performance Liquid Chromatograph | | |
|---|---|---|---|
| Chromatographic column | Waters Xbridge C18 (4.6 mm × 150 mm, 3.5 μm) (PDS-HPLC-154) | | |
| Mobile phase A | 0.1% TFA aqueous solution | | |
| Mobile phase B | Acetonitrile solution | | |
| Flow rate | 1 mL/min | | |
| Sampling volume | 10 μl | | |
| Detecting wavelength | 220 nm, 280 nm/full wave length | | |
| Column temperature | 35° C. | | |
| Diluent | Acetonitrile: Water (30:10) | | |
| Gradient elution procedure | Time (min) | Mobile phase A (%) | Mobile phase B (%) |
| | 0 | 100 | 0 |
| | 15 | 60 | 40 |
| | 30 | 45 | 55 |
| | 40 | 5 | 95 |
| | 45 | 5 | 95 |
| | 47 | 100 | 0 |
| | 55 | 100 | 0 |

Conclusion: The amount of total impurity of Crystal Form A of Compound 1 did not increase, indicating good physical stability.

Experimental Example 2

S1P1 Receptor Agonistic Activity Test

I. Cells Treatment
1. PathHunter cell line was thawed according to standard procedures.
2. The cells were inoculated in 20 μl 384-well microplates and incubated at 37° C. for appropriate time.

II. Agonist
1. For the agonist assay, the cells were incubated with the testing sample to induce the reaction.
2. The stock solution had been diluted 5 times with the buffer.
3. 5 μl of 5-fold dilution was added into the cells, which were incubated at 37° C. for 90-180 min with the vehicle concentration of 1%.

III. Signal Detection
1. 12.5 μl or 15 μl of PathHunter detection reagent at a volume ratio of 50% was added in one portion, then incubation at room temperature was performed for 1 h to generate detection signal.
2. The PerkinElmer Envision™ instrument was used to read the microplate for chemiluminescence signal detection.

IV. Data Analysis
1. CBIS data analysis kit was used to analyze the activity of the compound.
2. Calculation formula:

% Activity=100%×(average RLU of testing sample−average RLU of vehicle)/(average RLU of maximum control ligand−average RLU of vehicle)

The results were shown in Table 3.

TABLE 3

S1P1 receptor agonistic activity test results

| Testing Sample | S1P1 Receptor agonistic activity |
|---|---|
| Compound 1 | <10 nM |

Conclusion: Compound 1 has significant and unexpected receptor agonistic activity.

Experimental Example 3

Pharmacokinetic Evaluation of the Compounds

This Example is provided to test pharmacokinetics of compounds in SD rats.

Materials: Sprague Dawley rats (male, 200-300 g, 7-9 weeks, Shanghai SLAC)

Procedures: The rodent pharmacokinetic characteristics of the compound after intravenous injection and oral administration were tested according to standard protocol. In the test, the candidate compound was formulated as a clear solution, and the rats were given a single intravenous injection and oral administration. The intravenous and oral vehicles were a hydroxypropyl β cyclodextrin aqueous solution in a certain proportion or normal saline solution. The whole blood sample within 24 h was collected, centrifuged at 3000 g for 15 min, and the supernatant was separated to give the plasma sample. 4 volumes of acetonitrile solution containing internal standard was added to precipitate protein and after centrifugation the supernatant was collected and added with equal volume of water. After further centrifugation, the supernatant was used for injection. Quantitative analysis of blood drug concentration was done by LC-MS/MS analysis method and pharmacokinetic parameters were calculated, such as $C_{max}$, $T_{max}$, clearance, half-life, area under the curve of drug concentration-time, bioavailability, etc.

The results were shown in Table 4.

TABLE 4

Pharmacokinetic test results

| Testing Sample | Clearance (mL/min/kg) | Half-life $T_{1/2}$ (h) | Concentration Integration AUC (nM · hr) | Bioavailability F (%) |
|---|---|---|---|---|
| Ozanimod (3 mpk) | 46.3 | 5.24 | 1123 | 41.6 |
| Compound 1 | 11.5 | 3.46 | 6825 | 85.8 |

Conclusion: Compound 1 can significantly improve one or more indicators of rat pharmacokinetics compared to Ozanimod.

Experimental Example 4

Effects of Single Oral Administration on Blood Lymphocytes in Rats

Normal SPF grade male SD rats were administered by single oral gavage. The experiment contained five groups: the vehicle control group, the reference compound Ozanimod group, Compound 1-0.3 mg/kg dose group, Compound 1-1.0 mg/kg dose group, Compound 1-3 mg/kg dose group. Blood was collected 0.5 h before administration and 4, 8, 24 h after administration, and anticoagulated with 10% $K_2$-EDTA. The anticoagulated blood sample was placed in 4° C. environment, diluted 1:4 with normal saline, and quickly tested with a hematology analyzer to calculate the number of lymphocytes per liter of blood and the percentage in the total white blood cells. Graphpad prism 6.0 software was used to calculate the mean±standard error, and the two-way ANOVA test was used to test the significance of the difference. When p<0.05, there was a significant difference between two groups.

After single oral administration, the number of blood lymphocytes at 1.0 mg/kg of Ozanimod and 0.3, 1.0 and 3.0 mg/kg of Compound 1 reached the maximum decreasing rate at 8 h, which were 84.39%, 66.87%, 83.09% and 85.92%, respectively. Compound 1 significantly reduced the number of blood lymphocytes at all three concentrations. As compared with the vehicle control group, for the low dose group, P<0.001, and for Compound 1 medium and high dose groups, P<0.0001. Ozanimod at 1.0 mg/kg and Compound 1 at 0.3, 1.0 and 3.0 mg/kg had blood lymphocyte decreasing rates at 24 h of 47.26%, −44.98%, 0.22% and 55.15%, respectively. Compound 1 had a trend of dose-effect dependence (p<0.05 in the comparison of the high dose group with the low dose group), and was significantly different from Ozanimod group (p<0.0001 in the comparison of the low dose group with Ozanimod group; and P<0.05 in the comparison of the medium dose group with Ozanimod group).

With respect to Compound 1, at the doses of 0.3 mg/kg, 1 mg/kg and 3 mg/kg, the percentage of lymphocytes decreased significantly at 4 and 8 h after administration, and reaches the lowest at 8 h. At 24 h after administration, the percentage of lymphocytes in each group returned to the levels prior to administration. Compared to Ozanimod at 1 mg/kg group, there was no significant difference for Compound 1 in the percentage of blood lymphocytes in rats at each time point after administration.

TABLE 5

Rate of change of lymphocytes in blood after administration (%) (mean ± SEM)

| Time (h) | Vehicle control group (n = 8) | Ozanimod 1 mg/kg (n = 8) | Compound 1 0.3 mg/kg (n = 8) | Compound 1 1.0 mg/kg (n = 8) | Compound 1 3.0 mg/kg (n = 8) |
|---|---|---|---|---|---|
| 4 | −1.79 ± 8.29 | −71.79 ± 2.51**** | −59.57 ± 2.01**** | −71.25 ± 1.93**** | −78.97 ± 0.91**** |
| 8 | −22.18 ± 6.50 | −84.39 ± 1.16**** | −66.87 ± 1.97*** | −83.09 ± 1.25**** | −85.92 ± 1.26**** |
| 24 | 30.03 ± 10.40 | −47.26 ± 4.34**** | 44.98 ± 16.62#### | −0.22 ± 6.87**#$$ | −55.15 ± 3.32*****$$$$& |

Note:
a. Rate of decrease was calculated compared to the number of lymphocytes in the same group before administration.
b. Two way ANOVA test, Tukey multiple comparison method:
**p < 0.01,
***p < 0.001,
****p < 0.0001 vs. Vehicle control group;
p < 0.05,
p < 0.0001 vs. Ozanimod group;
$$p < 0.01,
$$$$p < 0.001 vs. Compound 1 −0.3 mg/kg group;
&p < 0.05 vs. Compound 1 −1.0 mg/kg group.

TABLE 6

Percentage of lymphocytes in white blood cells in a unit volume of blood (%) (mean ± SEM, n = 8)

| Time (h) | Vehicle control group (n = 8) | Ozanimod 1 mg/kg (n = 8) | Compound 1 0.3 mg/kg (n = 8) | Compound 1 1.0 mg/kg (n = 8) | Compound 1 3.0 mg/kg (n = 8) |
|---|---|---|---|---|---|
| −0.5 | 61.18 ± 2.72 | 58.67 ± 1.61 | 59.12 ± 2.19 | 59.49 ± 1.01 | 62.35 ± 2.26 |
| 4 | 60.00 ± 2.63 | 44.53 ± 3.75*** | 52.08 ± 3.35&&& | 36.82 ± 2.33****$$$ | 34.03 ± 3.81****#$$$$ |

TABLE 6-continued

Percentage of lymphocytes in white blood cells in a unit volume of blood (%) (mean ± SEM, n = 8)

| Time (h) | Vehicle control group (n = 8) | Ozanimod 1 mg/kg (n = 8) | Compound 1 0.3 mg/kg (n = 8) | Compound 1 1.0 mg/kg (n = 8) | Compound 1 3.0 mg/kg (n = 8) |
|---|---|---|---|---|---|
| 8 | 58.12 ± 1.70 | 35.69 ± 2.47****$ | 46.71 ± 3.72*#&&&& | 29.89 ± 2.56****$$$$ | 26.19 ± 2.81****$$$$ |
| 24 | 60.80 ± 1.73 | 58.63 ± 2.17 | 63.86 ± 1.70 | 61.62 ± 1.61 | 57.05 ± 2.49 |

Note:
Two way ANOVA test, Tukey multiple comparison method:
*$p < 0.05$,
***$p < 0.001$,
****$p < 0.0001$ vs. Vehicle control group;
$p < 0.05$ vs. Ozanimod group;
$$$$p < 0.001$,
$$$$$p < 0.0001$ vs Compound 1 –0.3 mg/kg group;
&&&$p < 0.001$,
&&&&$p < 0.0001$ vs. Compound 1 –1.0 mg/kg group.

Conclusion: The above results suggested that, in normal rats, single oral administration of Compound 1 can significantly reduce the number of lymphocytes in the peripheral blood and the percentage of lymphocytes in the white blood cells in a dose-effect relationship. At doses as low as 0.3 mg/kg, it had significant effect of reducing the number of blood lymphocytes. The number of lymphocytes recovered faster than that of Ozanimod at 24 h ($p<0.05$ compared to the same dose). At the same dose (1.0 mg/kg), the percentage of blood lymphocytes in rats was comparable to that of Ozanimod.

Experimental Example 5

Pharmacodynamic Test on TNBS-Induced Acute Infectious Bowel Disease (IBD) Model in Female SD Rats Female SD rats were divided into 7 groups, that is, model group, prednisolone-10 mg/kg group, Ozanimod-0.3 mg/kg group, Ozanimod-1.0 mg/kg group, Compound 1-0.1 mg/kg group, Compound 1-0.3 mg/kg group, Compound 1-0.6 mg/kg group. All animals were deeply anesthetized with pentobarbital sodium, and TNBS-50% alcohol solution was inserted into the intestinal cavity from the anus for modeling. The animal's anus was squeezed, and the animal was allowed to stand upside down for 5 min. The animals were returned to the cage after assured to be leak free.

The test compounds were administered orally 1 h after modeling, once a day for 7 days. The model group was given an equal volume of drug vehicle. The animals were weighed daily before administration of the test compound and were monitored for daily fecal traits and given clinical observation scores. The day after the last administration, all animals were euthanized. The colons were collected (anal to nodular part), the length and weight of the colons were measured, and the gross anatomical scores of the lesion sizes was taken. The gross anatomical images of the colon lesions were recorded, and the tissues were fixed in 10% neutral formalin solution and were subjected to histopathological analysis. Compound 1-0.6 mg/kg dose group showed a significant therapeutic effect on the area of colon injury. The measured data was 3.42 $cm^2$, which was significantly reduced compared to the model group (5.68 $cm^2$) and was superior over prednisolone-10 mg/kg group and Ozanimod-1.0 mg/kg for therapeutic effect.

The histological test results showed that, the infiltration degree of intestinal mucositis cells in Compound 1-0.6 mg/kg group was reduced, and the ulcer score, inflammation score and total injury score were 2.00, 3.29 and 5.29, respectively, which were significantly reduced compared to the model group (3.29, 4.43 and 7.71), comparable to the therapeutic effect of the prednisolone-10 mg/kg group, and superior over the therapeutic effect of the Ozanimod-1.0 mg/kg group. According to dissection at the end of the experiment, the symptoms of colon ulcers and edema in the Compound 1-0.6 mg/kg treatment group were all reduced compared to the model group. The colon ulcers in the prednisolone-10 mg/kg group were not reduced, and the edema area showed a tendency to decrease. No significant difference in colon weight and weight-to-length ratio was observed in all the groups when compared to the model group.

TABLE 7

Colon injury, ulcer area in each group (mean ± sem)

| Group | Animal | Injury area ($cm^2$) | Ulcer area ($cm^2$) |
|---|---|---|---|
| Model group | 7 | 5.68 ± 0.67 | 2.31 ± 0.65 |
| Prednisolone 10 mg/kg | 8 | 4.45 ± 0.82 | 1.58 ± 0.53 |
| Ozanimod 0.3 mg/kg | 7 | 4.76 ± 0.33 | 1.12 ± 0.31 |
| Ozanimod 1.0 mg/kg | 7 | 4.60 ± 0.71 | 1.36 ± 0.48 |
| Compound 1 0.1 mg/kg | 7 | 6.09 ± 0.94 | 2.42 ± 0.66 |
| Compound 1 0.3 mg/kg | 7 | 5.34 ± 0.90 | 2.18 ± 0.84 |
| Compound 1 0.6 mg/kg | 7 | 3.42 ± 0.73* | 0.94 ± 0.55 |

T-test: *$p < 0.05$ vs. model group

TABLE 8

Colon pathological test (mean ± sem)

| Group | Animals | Ulcer score | Inflammation score | Total injury score |
|---|---|---|---|---|
| Model Group | 7 | 3.29 ± 0.18 | 4.43 ± 0.30 | 7.71 ± 0.42 |
| Prednisolone –10 mg/kg | 8 | 2.00 ± 0.38** | 3.00 ± 0.33** | 5.00 ± 0.63** |
| Ozanimod –0.3 mg/kg | 7 | 2.57 ± 0.37 | 3.71 ± 0.42 | 6.29 ± 0.75 |
| Ozanimod –1.0 mg/kg | 7 | 2.57 ± 0.30* | 3.43 ± 0.30* | 6.00 ± 0.58* |

TABLE 8-continued

| | Colon pathological test (mean ± sem) | | | |
|---|---|---|---|---|
| Group | Animals | Ulcer score | Inflammation score | Total injury score |
| Compound 1 –0.1 mg/kg | 7 | 2.57 ± 0.20* | 3.57 ± 0.20* | 6.14 ± 0.40* |
| Compound 1 –0.3 mg/kg | 7 | 2.57 ± 0.30 | 3.57 ± 0.37 | 6.14 ± 0.63 |
| Compound 1 –0.6 mg/kg | 7 | 2.00 ± 0.38** | 3.29 ± 0.42* | 5.29 ± 0.78* |

T-test: *p < 0.05 vs. model group;
**p < 0.01 vs. model group

Conclusion: In this study, Compound 1 at a dose of 0.6 mg/kg can significantly reduce ulcer and inflammation conditions in the TNBS-induced acute colitis model rats for therapeutic effect, which was comparable to the therapeutic effect of prednisolone-10 mg/kg group, and was superior over the therapeutic effect of Ozanimod-1.0 mg/kg.

The invention claimed is:

1. A Crystal Form A of Compound 1, wherein
the Crystal Form A has an X-ray powder diffraction pattern having characteristic diffraction peaks at the following 2θ angles: 6.66±0.2°, 13.30±0.2°, 15.57±0.2°

Compound 1

2. The Crystal Form A of Compound 1 according to claim 1, wherein
the Crystal Form A has an X-ray powder diffraction pattern having characteristic diffraction peaks at the following 2θ angles: 6.66±0.2°, 13.30±0.2°, 14.46±0.2°, 15.57±0.2°, 19.99±0.2°, 21.83±0.2°, 24.41±0.2°, 25.26±0.2°.

3. The Crystal Form A of Compound 1 according to claim 2, wherein
the Crystal Form A has an X-ray powder diffraction pattern having characteristic diffraction peaks at the following 2θ angles: 6.66±0.2°, 12.21±0.2°, 13.30±0.2°, 14.46±0.2°, 15.57±0.2°, 16.77±0.2°, 19.99±0.2°, 21.83±0.2°, 24.41±0.2°, 25.26±0.2°, 27.20±0.2°.

4. The Crystal Form A of Compound 1 according to claim 3, wherein
the Crystal Form A has an X-ray powder diffraction pattern as shown in FIG. 1.

5. The Crystal Form A of Compound 1 according to claim 1, wherein
the Crystal Form A has a differential scanning calorimetry curve having onset point of endothermic peak at 199.27° C.±2° C.

6. The Crystal Form A of Compound 1 according to claim 5, wherein
the Crystal Form A has a DSC pattern as shown in FIG. 2.

7. The Crystal Form A of Compound 1 according to claim 1, wherein
the Crystal Form A has a thermogravimetric analysis curve, wherein no significant weight loss occurs prior to 251.39° C., and decomposition occurs after 251.39° C.

8. The Crystal Form A of Compound 1 according to claim 7, wherein
the Crystal Form A has a TGA pattern as shown in FIG. 3.

9. A process for preparing the Crystal Form A, according to claim 1, comprising
adding the Compound 1 into acetonitrile, an alcohol solvent, a ketone solvent, an ester solvent, an ether solvent, a mixed solvent of alcohol solvent and water, a mixed solvent of acetonitrile and water, a mixed solvent of ketone solvent and water, or a mixed solvent of ether solvent and water; and
recrystallizing or slurrying to obtain the Crystal Form A.

10. The process for preparing the Crystal Form A according to claim 9, wherein
the alcohol solvent is selected from the group consisting of methanol, ethanol and isopropanol.

11. The process for preparing the Crystal Form A according to claim 9, wherein
the ketone solvent is selected from the group consisting of acetone and butanone.

12. The process for preparing the Crystal Form A according to claim 9, wherein
the ether solvent is selected from the group consisting of ethylene glycol dimethyl ether.

13. The process for preparing the Crystal Form A according to claim 9, wherein
the ester solvent is selected from the group consisting of ethyl acetate.

14. The process for preparing the Crystal Form A according to claim 9, wherein
the mixed solvent of alcohol solvent and water is a mixed solvent of ethanol and water, a mixed solvent of methanol and water, or a mixed solvent of isopropanol and water.

15. The process for preparing the Crystal Form A according to claim 9, wherein
the mixed solvent of ketone solvent and water is selected from the group consisting of a mixed solvent of acetone and water.

16. The process for preparing the Crystal Form A according to claim 14, wherein
in the mixed solvent of alcohol solvent and water, the volume ratio of alcohol solvent to water is selected from the group consisting of 1:0.2-1.5.

17. The process for preparing the Crystal Form A according to claim 15, wherein
in the mixed solvent of ketone solvent and water, the volume ratio of ketone solvent to water is selected from the group consisting of 1:0.3-0.8.

18. The process for preparing the Crystal Form A according to claim 9, wherein
in the mixed solvent of acetonitrile and water, the volume ratio of acetonitrile to water is selected from the group consisting of 1:0.5-1.5.

19. A method for treating a disease associated with S1P1 receptor, wherein the disease associated with S1P1 receptor is inflammatory bowel disease, comprising administrating the Crystal Form A of Compound 1 according claim 1 to a subject in need thereof.

\* \* \* \* \*